United States Patent
Yamanaka et al.

(10) Patent No.: US 9,060,687 B2
(45) Date of Patent: Jun. 23, 2015

(54) DEVICE FOR MONITORING BLOOD VESSEL CONDITIONS AND METHOD FOR MONITORING SAME

(75) Inventors: Mikihiro Yamanaka, Osaka (JP); Megumi Hijikuro, Osaka (JP); Keita Hara, Osaka (JP)

(73) Assignee: SHARP KABUSHIKI KAISHA, Osaka (JP)

( * ) Notice: Subject to any disclaimer, the term of this patent is extended or adjusted under 35 U.S.C. 154(b) by 133 days.

(21) Appl. No.: 13/499,226

(22) PCT Filed: Oct. 1, 2010

(86) PCT No.: PCT/JP2010/067254
§ 371 (c)(1),
(2), (4) Date: Mar. 29, 2012

(87) PCT Pub. No.: WO2011/040599
PCT Pub. Date: Apr. 7, 2011

(65) Prior Publication Data
US 2012/0190945 A1  Jul. 26, 2012

(30) Foreign Application Priority Data
Oct. 2, 2009  (JP) .................................. 2009-230686

(51) Int. Cl.
*A61B 5/00* (2006.01)
*A61B 5/02* (2006.01)
(Continued)

(52) U.S. Cl.
CPC ............ *A61B 5/0059* (2013.01); *A61B 5/0071* (2013.01); *A61B 5/02007* (2013.01); *A61B 5/14546* (2013.01); *A61B 5/1455* (2013.01); *A61B 5/4866* (2013.01); *A61B 5/6824* (2013.01);
(Continued)

(58) Field of Classification Search
CPC ........................................................ A61B 5/00
USPC .................................................. 600/473–478
See application file for complete search history.

(56) References Cited

U.S. PATENT DOCUMENTS 5,624,804 A  4/1997  Bucala
5,629,408 A  5/1997  Bucala
(Continued)

FOREIGN PATENT DOCUMENTS

JP   2-203255 A   8/1990
JP   7-502534 A   3/1995
(Continued)

OTHER PUBLICATIONS

English translation of an International Preliminary Report on Patentability for International Application No. PCT/JP2010/067254, dated May 18, 2012.
(Continued)

*Primary Examiner* — Peter Luong
(74) *Attorney, Agent, or Firm* — Birch, Stewart, Kolasch & Birch, LLP

(57) ABSTRACT

The present invention detects a fluorescent signal from AGEs at a blood vessel tissue of an individual to determine the condition of the tissue of the individual. This solves a problem that in measurement of AGEs used in diagnosis of diabetes, data indicative of fluorescent spectrum from AGEs at the skin of a forearm varies depending on where to measure on skin of even the same forearm, which results in variations in measurement values, leading to unreliable data and incorrect measurement result.

15 Claims, 8 Drawing Sheets

(51) Int. Cl.
    *A61B 5/145*       (2006.01)
    *A61B 5/1455*      (2006.01)

(52) U.S. Cl.
    CPC ......... *A61B 5/6825* (2013.01); *A61B 2562/185* (2013.01)

(56) References Cited

U.S. PATENT DOCUMENTS

| | | | |
|---|---|---|---|
| 5,655,530 A | 8/1997 | Messerschmidt | |
| 5,683,887 A | 11/1997 | Bucala | |
| 5,702,704 A | 12/1997 | Bucala | |
| 5,712,101 A | 1/1998 | Bucala | |
| 5,733,546 A | 3/1998 | Bucala | |
| 5,823,951 A | 10/1998 | Messerschmidt | |
| 6,061,583 A | 5/2000 | Ishihara et al. | |
| 6,070,093 A | 5/2000 | Oosta et al. | |
| 6,094,300 A | 7/2000 | Kashima et al. | |
| 6,115,673 A | 9/2000 | Malin et al. | |
| 6,152,876 A | 11/2000 | Robinson et al. | |
| 6,212,424 B1 | 4/2001 | Robinson | |
| 6,240,306 B1 | 5/2001 | Rohrscheib et al. | |
| 6,292,686 B1 | 9/2001 | Chaiken et al. | |
| 6,349,227 B1 | 2/2002 | Numada | |
| 6,389,306 B1 | 5/2002 | Chaiken et al. | |
| 6,411,373 B1 | 6/2002 | Garside et al. | |
| 6,415,167 B1 | 7/2002 | Blank et al. | |
| 6,505,059 B1 | 1/2003 | Kollias et al. | |
| 6,534,012 B1 | 3/2003 | Hazen et al. | |
| 6,567,678 B1 | 5/2003 | Oosta et al. | |
| 6,622,032 B1 | 9/2003 | Robinson et al. | |
| 6,865,408 B1 | 3/2005 | Abbink et al. | |
| 6,871,169 B1 | 3/2005 | Hazen et al. | |
| 2001/0018560 A1 | 8/2001 | Robinson | |
| 2002/0016534 A1 | 2/2002 | Trepagnier et al. | |
| 2002/0035341 A1 | 3/2002 | Rohrscheib et al. | |
| 2002/0038080 A1 | 3/2002 | Makarewicz et al. | |
| 2002/0082487 A1 | 6/2002 | Kollias et al. | |
| 2002/0091324 A1 | 7/2002 | Kollias et al. | |
| 2002/0099278 A1 | 7/2002 | Makarewicz et al. | |
| 2002/0174318 A1 | 11/2002 | Stuttard et al. | |
| 2003/0007147 A1 | 1/2003 | Johnson | |
| 2003/0023152 A1 | 1/2003 | Abbink et al. | |
| 2003/0023170 A1 | 1/2003 | Gardner et al. | |
| 2003/0069484 A1 | 4/2003 | Blank et al. | |
| 2003/0152947 A1 | 8/2003 | Crossman et al. | |
| 2003/0191378 A1 | 10/2003 | Davis, III et al. | |
| 2003/0208111 A1 | 11/2003 | Mattu et al. | |
| 2003/0216627 A1 | 11/2003 | Lorenz et al. | |
| 2004/0024553 A1 | 2/2004 | Monfre et al. | |
| 2004/0039271 A1 | 2/2004 | Blank et al. | |
| 2004/0068163 A1 | 4/2004 | Ruchti et al. | |
| 2004/0082070 A1 | 4/2004 | Jones et al. | |
| 2004/0127777 A1 | 7/2004 | Ruchti et al. | |
| 2004/0167382 A1 | 8/2004 | Gardner et al. | |
| 2004/0215066 A1 | 10/2004 | Huang et al. | |
| 2004/0235161 A1 | 11/2004 | Tabata et al. | |
| 2004/0239461 A1 | 12/2004 | Kincaid et al. | |
| 2004/0267105 A1 | 12/2004 | Monfre et al. | |
| 2005/0010090 A1 | 1/2005 | Acosta et al. | |
| 2005/0014997 A1 | 1/2005 | Ruchti et al. | |
| 2005/0020892 A1 | 1/2005 | Acosta et al. | |
| 2005/0049466 A1 | 3/2005 | Blank et al. | |
| 2005/0054908 A1 | 3/2005 | Blank et al. | |
| 2005/0090750 A1 | 4/2005 | Ediger et al. | |
| 2005/0107676 A1 | 5/2005 | Acosta et al. | |
| 2005/0119541 A1 | 6/2005 | Lorenz et al. | |
| 2005/0148834 A1 | 7/2005 | Hull et al. | |
| 2005/0149300 A1 | 7/2005 | Ruchti et al. | |
| 2005/0159656 A1 | 7/2005 | Hockersmith et al. | |
| 2005/0187439 A1 | 8/2005 | Blank et al. | |
| 2005/0196821 A1 | 9/2005 | Monfre et al. | |
| 2005/0203358 A1 | 9/2005 | Monfre et al. | |
| 2005/0203359 A1 | 9/2005 | Blank et al. | |
| 2005/0203364 A1 | 9/2005 | Monfre et al. | |
| 2005/0209514 A1 | 9/2005 | Oshima et al. | |
| 2005/0209515 A1 | 9/2005 | Hockersmith et al. | |
| 2005/0211872 A1 | 9/2005 | Kawano et al. | |
| 2005/0240090 A1 | 10/2005 | Ruchti et al. | |
| 2005/0261560 A1 | 11/2005 | Ridder et al. | |
| 2005/0267341 A1 | 12/2005 | Blank et al. | |
| 2005/0267342 A1 | 12/2005 | Blank et al. | |
| 2006/0116562 A1 | 6/2006 | Acosta et al. | |
| 2006/0167349 A1 | 7/2006 | Gardner et al. | |
| 2006/0173254 A1 | 8/2006 | Acosta et al. | |
| 2006/0173255 A1 | 8/2006 | Acosta et al. | |
| 2006/0173256 A1 | 8/2006 | Ridder et al. | |
| 2006/0178570 A1 | 8/2006 | Robinson et al. | |
| 2006/0183983 A1 | 8/2006 | Acosta et al. | |
| 2006/0195022 A1 | 8/2006 | Trepangnier et al. | |
| 2006/0195023 A1 | 8/2006 | Acosta et al. | |
| 2006/0200017 A1 | 9/2006 | Monfre et al. | |
| 2006/0206018 A1 | 9/2006 | Abul-Haj et al. | |
| 2006/0211927 A1 | 9/2006 | Acosta et al. | |
| 2006/0211928 A1* | 9/2006 | Hull et al. ..................... 600/317 |
| 2006/0211931 A1 | 9/2006 | Blank et al. | |
| 2006/0217602 A1 | 9/2006 | Abul-Haj et al. | |
| 2006/0244186 A1 | 11/2006 | Wells | |
| 2007/0038046 A1 | 2/2007 | Hayter | |
| 2007/0038116 A1 | 2/2007 | Yamanaka et al. | |
| 2007/0053940 A1 | 3/2007 | Huang et al. | |
| 2007/0073118 A1 | 3/2007 | Ridder et al. | |
| 2007/0088205 A1 | 4/2007 | Hull et al. | |
| 2007/0142720 A1 | 6/2007 | Ridder et al. | |
| 2007/0142727 A1 | 6/2007 | Zhang et al. | |
| 2007/0149868 A1 | 6/2007 | Blank et al. | |
| 2007/0179367 A1 | 8/2007 | Ruchti et al. | |
| 2007/0193879 A1 | 8/2007 | Prengaman et al. | |
| 2007/0197880 A1 | 8/2007 | Maynard et al. | |
| 2007/0226458 A1 | 9/2007 | Stuttard et al. | |
| 2007/0234300 A1 | 10/2007 | Leake et al. | |
| 2007/0242074 A1 | 10/2007 | Stuttard et al. | |
| 2007/0245123 A1 | 10/2007 | Stuttard et al. | |
| 2007/0245130 A1 | 10/2007 | Stuttard et al. | |
| 2007/0245132 A1 | 10/2007 | Stuttard et al. | |
| 2007/0265532 A1 | 11/2007 | Maynard et al. | |
| 2007/0276199 A1 | 11/2007 | Ediger et al. | |
| 2007/0293743 A1 | 12/2007 | Monfre et al. | |
| 2007/0293744 A1 | 12/2007 | Monfre et al. | |
| 2007/0294510 A1 | 12/2007 | Stuttard et al. | |
| 2008/0007562 A1 | 1/2008 | Stuttard et al. | |
| 2008/0008393 A1 | 1/2008 | Stuttard et al. | |
| 2008/0010436 A1 | 1/2008 | Stuttard et al. | |
| 2008/0016318 A1 | 1/2008 | Stuttard et al. | |
| 2008/0028184 A1 | 1/2008 | Stuttard et al. | |
| 2008/0033275 A1 | 2/2008 | Blank et al. | |
| 2008/0034185 A1 | 2/2008 | Stuttard et al. | |
| 2008/0034186 A1 | 2/2008 | Stuttard et al. | |
| 2008/0040575 A1 | 2/2008 | Stuttard et al. | |
| 2008/0052492 A1 | 2/2008 | Stuttard et al. | |
| 2008/0097174 A1 | 4/2008 | Maynard et al. | |
| 2008/0098201 A1 | 4/2008 | Stuttard et al. | |
| 2008/0103373 A1 | 5/2008 | Matter et al. | |
| 2008/0103396 A1 | 5/2008 | Johnson et al. | |
| 2008/0132793 A1 | 6/2008 | Kollias et al. | |
| 2008/0146899 A1 | 6/2008 | Ruchti et al. | |
| 2008/0162874 A1 | 7/2008 | Stuttard et al. | |
| 2008/0162875 A1 | 7/2008 | Stuttard et al. | |
| 2008/0184017 A1 | 7/2008 | Stuttard et al. | |
| 2008/0199865 A1 | 8/2008 | Crossman et al. | |
| 2008/0208018 A1 | 8/2008 | Ridder et al. | |
| 2008/0221066 A1 | 9/2008 | Holmberg et al. | |
| 2008/0319286 A1 | 12/2008 | Ridder et al. | |
| 2008/0319299 A1 | 12/2008 | Stippick et al. | |
| 2008/0319382 A1 | 12/2008 | Blank et al. | |
| 2009/0003764 A1 | 1/2009 | Ridder et al. | |
| 2009/0018415 A1 | 1/2009 | Robinson et al. | |
| 2009/0041567 A1 | 2/2009 | Wells | |
| 2009/0198898 A1 | 8/2009 | Stuttard et al. | |
| 2009/0228683 A1 | 9/2009 | Stuttard et al. | |
| 2009/0234204 A1 | 9/2009 | Ridder et al. | |
| 2009/0247840 A1 | 10/2009 | Blank et al. | |
| 2009/0318786 A1 | 12/2009 | Blank et al. | |
| 2010/0010325 A1 | 1/2010 | Ridder et al. | |

(56) References Cited

U.S. PATENT DOCUMENTS

| | | |
|---|---|---|
| 2010/0286529 A1 | 11/2010 | Carroll et al. |
| 2011/0178397 A1* | 7/2011 | Bahner ............... 600/431 |
| 2011/0178420 A1 | 7/2011 | Ridder et al. |
| 2011/0184260 A1 | 7/2011 | Robinson et al. |
| 2011/0270092 A1* | 11/2011 | Kang et al. .............. 600/476 |
| 2011/0282167 A1 | 11/2011 | Ridder et al. |
| 2012/0065484 A1 | 3/2012 | Hull et al. |
| 2012/0078075 A1 | 3/2012 | Maynard et al. |
| 2012/0078473 A1 | 3/2012 | Ridder et al. |

FOREIGN PATENT DOCUMENTS

| | | | |
|---|---|---|---|
| JP | 8-117209 A | 5/1996 |
| JP | 8-252246 A | 10/1996 |
| JP | 10-10049 A | 1/1998 |
| JP | 10-206742 A | 8/1998 |
| JP | 11-231227 A | 8/1999 |
| JP | 2000-189391 A | 7/2000 |
| JP | 2000-329696 A | 11/2000 |
| JP | 2001-59814 | 3/2001 |
| JP | 2001-87249 A | 4/2001 |
| JP | 2001-524342 A | 12/2001 |
| JP | 2002-510515 A | 4/2002 |
| JP | 2002-512830 A | 5/2002 |
| JP | 2002-291722 A | 10/2002 |
| JP | 2003-52699 A | 2/2003 |
| JP | 2005-500032 A | 1/2005 |
| JP | 2005-49238 A | 2/2005 |
| JP | 2005-185575 A | 7/2005 |
| JP | 2005-296635 A | 10/2005 |
| JP | 2005-301065 A | 10/2005 |
| JP | 2006-98340 A | 4/2006 |
| JP | 2006-102191 A | 4/2006 |
| JP | 2006-132995 A | 5/2006 |
| JP | 2006-235423 A | 9/2006 |
| JP | 2006-524544 A | 11/2006 |
| JP | 2007-44512 A | 2/2007 |
| JP | 2007-510159 A | 4/2007 |
| JP | 2007-222669 A | 9/2007 |
| JP | 2008-32703 A | 2/2008 |
| JP | 2008-51772 A | 3/2008 |
| JP | 2008-125989 A | 6/2008 |
| JP | 2008-531133 A | 8/2008 |
| JP | 2009-8460 A | 1/2009 |
| JP | 2009-47540 A | 3/2009 |
| JP | 2009-519779 A | 5/2009 |
| JP | 2010-2380 A | 1/2010 |
| JP | 2010-19579 A | 1/2010 |
| WO | WO 97/24066 A1 | 7/1997 |
| WO | WO 2008/107471 A2 | 9/2008 |

OTHER PUBLICATIONS

International Search Report for International Application No. PCT/JP2010/067254 dated Nov. 9, 2010.
International Search Report for corresponding International Application PCT/JP2010/070501 dated Mar. 29, 2011.
Masayoshi Takeuchi, "TAGE (toxic AGEs) hypothesis in life style-related disease" Hokuriku University, vol. 28, pp. 33-48, Oct. 2004.
"NEMOes, a new method to evaluate early atherosclerosis in rodent model", Hirotaka Watada Ryuzo Kawamori, Department of Medicine, Metabolism & Endocrinology, Juntendo University School of Medicine (Nov. 1, 2006) vol. 64, No. 11, pp. 2165-2175.
"Pathognostic Image Pattern of a Spectrum of Photosensitizers", Applied Physics (Oyou Butsuri), vol. 70, No. 6, p. 666-671 (Jun. 10, 2001), Katsuo Aizawa.
Office Action issued on Feb. 11, 2015 in co-pending U.S. Appl. No. 13/635,629.

* cited by examiner

FIG. 7

RELATION BETWEEN EXCITATION LIGHT SOURCE AND FLUORESCENT WAVELENGTH WITH RESPECT TO AGEs

| | EXCITATION LIGHT (Excitation)(nm) | FLUORESCENCE (Emission)(nm) |
|---|---|---|
| COLLAGEN-LINKED NORMAL FLUORESCENCE (CLF collagen-linked fluoescence) | 370 | 440 |
| PENTOSIDINE (Pentosidine) | 328 (ACID-HYDROLYZED :335) | 378 (ACID-HYDROLYZED :385) |
| VESPERLYSINES (Vesperlysines) | 370 | 440 | es # DEVICE FOR MONITORING BLOOD VESSEL CONDITIONS AND METHOD FOR MONITORING SAME

TECHNICAL FIELD

The present invention relates to a device and a method each for detecting fluorescence from a blood vessel of a living tissue and thus observing the health condition of the living body.

BACKGROUND ART

Recently, with westernization of diets, patients of lifestyle-related disease are increasing, resulting in serious medical and social problems. At present, in Japan, the number of diabetic patients is 8,000,000, and the number of diabetic patients plus pre-diabetic patients is 20,000,000. The three main complications of diabetes are retinopathy, nephropathy, and neuropathy. Diabetes is also a cause for arteriosclerosis. Furthermore, diabetes may cause heart diseases and brain diseases.

A person develops diabetes in such a manner that improper diets and life styles, secretion from fat cells due to fatness, or oxidative stress decrease the function of pancreas, causing shortage of insulin that controls blood glucose level or reducing the effect of insulin. Diabetes has symptoms such as frequent urination and increased amount of urination, and increased thirst. However, such symptoms may not enable patients to realize that they develop diabetes, and most patients know their illness when they are subjected to inspection in hospitals etc. This tells why there are so many "silent" diabetic patients. However, at the stage where abnormal symptoms resulting from the complications of diabetes are found in hospitals etc., conditions of the disease have advanced too far, making it difficult to completely cure the disease. In particular, many of the complications of diabetes are difficult to cure, and therefore prevention of diabetes is considered as important like many lifestyle-related diseases. For the prevention, early identification and early determination of therapeutic effect are essential, and there are many inspections for diabetes for this purpose.

When blood contains abnormal amounts of carbohydrates and lipids therein, oxidative stress causes a reaction with protein so that AGEs (Advanced Glycation Endproducts) are produced. AGEs are end products produced via nonenzymatic glycosylation reaction of protein (Maillard reaction). AGEs exhibit yellowish brown color, emit fluorescence, and form crosslink by binding to nearby proteins. AGEs are considered to be deposited on and infuse into blood vessel walls or interact with macrophage which is a part of an immune system to release cytokine which is a protein and to causes inflammation, resulting in arteriosclerosis.

In the case of diabetes, as the blood glucose level increases, the amount of AGEs increases. Accordingly, by monitoring AGEs, it is possible to identify diabetes at an early stage or comprehend progress of diabetes. One example of a method for screening diabetes mellitus by monitoring AGEs is a conventional art in Patent Literature 1. The conventional art of Patent Literature 1 uses a light source, a tissue sampling device, a detector, and a model used to connect detected fluorescence and the condition of the disease. In the conventional art, AGEs are monitored in such a manner that skin of a forearm is irradiated with excitation light and spectrum of fluorescence from AGEs binding to skin collagen is detected. Thus, data is obtained in a non-invasive manner.

CITATION LIST

Patent Literature

[Patent Literature 1]
Japanese Translation of PCT International Application, Tokuhyo No. 2007-510159 (published on Apr. 19, 2007)

SUMMARY OF INVENTION

Technical Problem

However, when spectrum of fluorescence from AGEs on skin of a forearm was obtained by using the system in Patent Literature 1, it was found that only a small amount of fluorescence was detected. This is because if where to measure is left to a user, the user does not consider the fact that fluorescent intensity varies greatly depending on whether a blood vessel exists or not and on what kind the blood vessel is. Furthermore, since where to measure is left to the user, the position of measurement varies with respect to each measurement. Since data varies depending on where to measure on skin of even the same forearm, variations in the position to be measured with respect to each measurement resulted in variations in measurement values. This raised a problem of unreliable data and incorrect measurement result.

Furthermore, a relation between measured AGEs binding to skin collagen and a specific disease is not clear, so that the measured data cannot be used effectively.

The present invention was made in view of the foregoing problem. An object of the present invention is to provide a device and a method each enabling any user to easily and daily monitor the user's health condition by detecting AGEs from blood vessel in a non-invasive manner and obtaining reliable data which is exact and well-related to vascular endothelial function.

Solution to Problem

A device of the present invention for monitoring blood vessel conditions includes: an excitation light source for exciting a blood vessel tissue of a living body; and a detecting section for detecting fluorescence from the blood vessel tissue excited by the excitation light source.

With the arrangement, the excitation light source irradiates the living body (or a part of the living body) including the blood vessel tissue with excitation light and the detecting section detects fluorescence from the excited blood vessel tissue.

There is a difference in fluorescent spectrum between, for example, AGEs accumulated at blood vessel walls and molecules constituting the blood vessels. Accordingly, in accordance with fluorescence detected by the detecting section, it is possible to determine whether AGEs are accumulated or not in the blood vessel tissue which emits the fluorescence. In this manner, AGEs can be detected from the blood vessel in a non-invasive manner, so that it is possible to detect AGEs from blood vessel tissues at every positions of the living body and to comprehend health conditions of blood vessels.

Advantageous Effects of Invention

Use of the device and method of the present invention for monitoring blood vessel conditions allows detecting AGEs from a blood vessel in a non-invasive manner and obtaining reliable data closely related to vascular endothelial functions, thereby allowing any user to easily and daily monitor health conditions of blood vessels. Accordingly, the present invention is highly expected to deal with cardiovascular function disorders such as diabetes and arteriosclerosis or motivate a user to deal with the cardiovascular function disorders.

BRIEF DESCRIPTION OF DRAWINGS

FIG. 7 is a table showing a relation between an excitation light source and fluorescent intensity with respect to AGEs.

DESCRIPTION OF EMBODIMENTS

Figure 1:
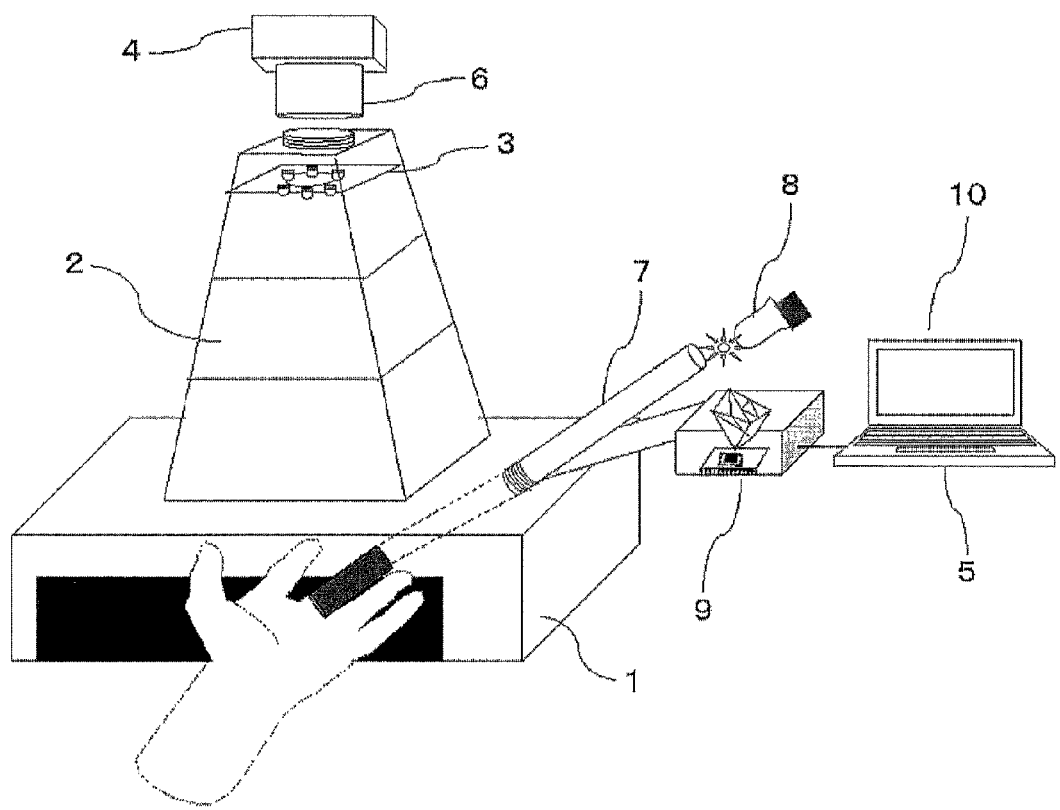
FIG. 1 is a view schematically showing a device for monitoring blood vessel conditions in accordance with an embodiment.

The following explains an embodiment of the present invention with reference to drawings. In the drawings, the same reference sign indicates the same part or a corresponding part. A device of the present invention for monitoring blood vessel conditions can be used by any user easily and with high precision for raising preventive attention against circulatory diseases. The device of the present invention includes an excitation light source for detecting fluorescence from AGEs and means for detecting the excited fluorescence.

At present, approximately 20 kinds of AGEs are known. Some of them emit fluorescence upon irradiation with excitation light. FIG. 7 is a table showing examples of AGEs. In the table, CLF (collagen-linked fluorescence) is fluorescence from AGEs binding to collagen, and is used as a general index for total production of AGEs and accompanying collagen crosslink.

Representative examples of AGEs are pentosidine and vesperlysine. Pentosidine is a fluorescent substance having a structure in which lysine and arginine each being equimolar to pentose are cross-linked with each other, and stable after acid hydrolysis. It is reported that pentosidine and vesperlysine increase in development of diabetes and the end stage of nephropathy. Vesperlysine is isolated as a main fluorescent material from acid-hydrolyzed AGE-bovine serum albumin (BSA), and has a structure in which two molecules of lysine are cross-linked with each other. The table of FIG. 7 shows a relation between the excitation light source and fluorescent intensity of AGEs.

As can be seen from the table of FIG. 7, the wavelength of the excitation light source is most preferably 370 nm or proximity thereof. Thus, the excitation light source whose wavelength is in the range of 365 to 370 nm or proximity thereof is particularly advantageous in terms of availability and safeness due to closeness to a visible region. However, the wavelength of the excitation light source is not limited to this. The appropriate wavelength range of the excitation light source set according to the kind of AGEs is 315 to 400 nm which is a UVA region or 315 to 600 nm which is a visible light region. In particular, the excitation wavelength in the range of 315 to 325 nm is advantageous since the excitation wavelength allows obtaining characteristic fluorescence from pentosidine which is a representative example of AGEs and which is closely related to nephropathy. The most suitable excitation wavelength is selected appropriately depending on what AGEs are to be detected.

It should be noted that when the excitation wavelength is longer than 500 to 600 nm, excited molecules are not prominent and consequently detection of fluorescence from AGEs is difficult. Accordingly, the excitation wavelength is preferably shorter than 500 to 600 nm.

Since fluorescence has a longer wavelength than excitation light, a detector used herein may be a one capable of detecting light in a range of 350 to 500 nm in consideration of the table of FIG. 7. For example, standard fine particles for fluorescent intensity correction manufactured by Moritex Corporation exhibit fluorescent wavelength of 510, 575, and 700 nm in response to excitation light of 488 nm, which shows that detected fluorescent wavelength varies according to the kind of AGEs. Accordingly, any detector is usable herein as long as the detector can detect fluorescence in a range of 320 to 900 nm.

By detecting fluorescence in this manner, it is possible to confirm AGEs from a blood vessel in a non-invasive manner.

Embodiment 1

FIG. 1 is a view showing a configuration of a device of the present invention for monitoring blood vessel conditions. The device includes a light-shielding case 1, a light-shielding cover 2 provided on the light-shielding case 1, a blood vessel visualizing light source 3 provided at the upper portion of the light-shielding cover 2, and a lens 6 and a blood vessel detecting device 4 each provided on the blood vessel light source 3. A cylindrical housing of the lens 6 has a pitch inside and a convex portion on the upper surface of the light-shielding cover 2 has a corresponding pitch, so that the lens 6 and the light-shielding cover 2 are formed integrally. A part of the light-shielding case 1 has a hole, optical fibers 7 are inserted into the hole from the outside of the light-shielding case 1, and one end of the optical fibers 7 (at the outside of the light-shielding case 1) is provided with an excitation light source 8. The detector 9 detects fluorescence. The optical fibers 7 include two kinds of fibers, an emitting fiber for emitting excitation light from the excitation light source 8 to the end of the fiber and a receiving fiber for receiving fluorescence from the end of the fiber to the detector 9. The two fibers are positioned concentrically and are separated from each other approximately at a position penetrating the upper surface of the light-shielding case 1.

Figure 2:
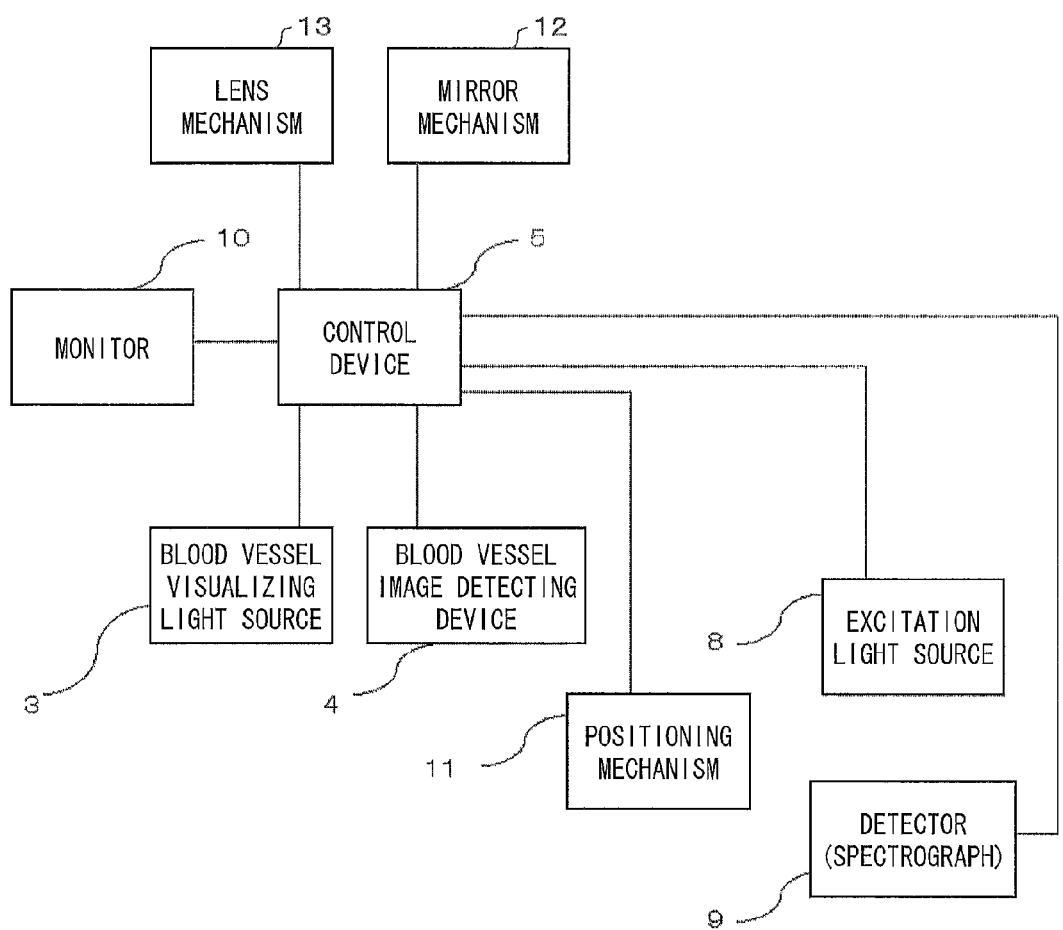
FIG. 2 is a view showing a configuration of the device for monitoring blood vessel conditions in accordance with the embodiment.

FIG. 2 is a view schematically showing the device for monitoring blood vessel conditions. The blood vessel visualizing light source 3, the blood vessel detecting device 4, the lens 6, the optical fibers 7, the excitation light source 8, the detector 9, and a mechanical positioning mechanism 11 are connected with a control device 5 so that they are controlled. A user can view the result of monitoring on a monitor 10.

Initially, a wrist, a finger, a palm etc. to be measured is inserted from the side of the light-shielding case 1 into the light-shielding case 1. The light-shielding case 1 is used to efficiently obtain fluorescence from a portion to be analyzed. The light-shielding case 1 may be made of any material including plastics such as light-shielding polystyrene and polyethylene, papers with aluminum foil inside the case, metals, and woods. In consideration of portability, economical efficiency, and durability, light-shielding plastics are advantageous. FIG. 1 shows a palm for convenience of explanation, but in reality the palm is not seen when it is inserted into the light-shielding case 1.

Like the light-shielding case 1, the light-shielding cover 2 is provided to efficiently obtain fluorescence from the portion to be analyzed. In consideration of portability and cost, the light-shielding cover 2 is preferably made of light-shielding plastics. Furthermore, if the light-shielding cover 2 is designed to consist of several units according to the magnification ratio of the later-mentioned lens 6, the light-shielding cover 2 has further portability because such units can be assembled together to form the light-shielding cover 2 only when needed and can be disassembled and stored when not used. It is desirable that the unit of the light-shielding cover 2 has a structure easily bindable to the light-shielding case 1, such as an inset structure.

Figure 3:
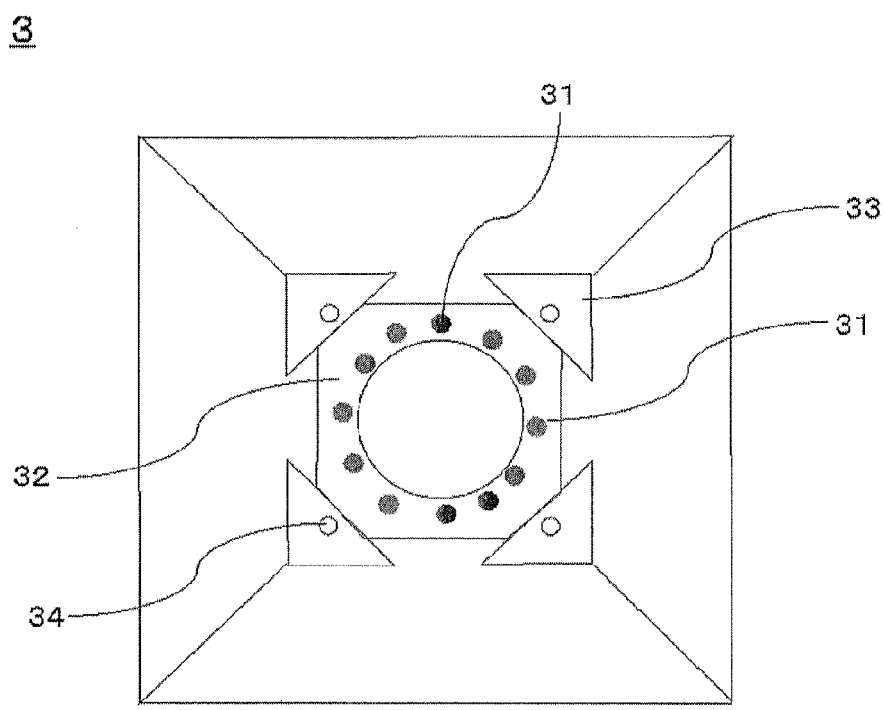
FIG. 3 is a view showing a layout of a light source of the device for monitoring blood vessel conditions in accordance with the embodiment.

FIG. 3 is a view explaining the blood vessel visualizing light source 3 in more details. FIG. 3 is a plane view of the blood vessel visualizing light source 3 inside the light-shielding cover 2 seen from below. The portion inserted into the light-shielding case 1 is irradiated with light from the blood vessel visualizing light source 3. Light sources 31 are mainly LEDs etc. The light sources 31 are positioned to surround a hole at the center of a substrate 32 in a donut-manner as shown in FIG. 3 for example. By positioning the light sources 31 in a donut-manner, it is possible for the blood vessel detecting device 4 above the blood vessel visualizing light source 3 to capture an image without the light sources 31 casting shadows. The substrate 32 is attached to the upper portion in the light-shielding cover 2 via a fixing washer 33 and a screw 34.

Subsequently, a blood vessel irradiated with light is detected by the blood vessel detecting device 4. The blood vessel detecting device is, for example, a camera having an image pickup device. Examples of the image pickup device include, but not limited to, CMOS (Complementary Metal Oxide Semiconductor) and CCD (Charge Coupled Device). Although not shown in the drawings, the image pickup device may be equipped, in front of pixels, with an IR cut filter for transmitting visible light and reflecting infrared. An image detected by the blood vessel detecting device 4 is displayed by the monitor 10 of the control device 5. By viewing the displayed image and operating the lens 6 connected with the blood vessel detecting device 4, the user can survey the position to be measured in a whole image or zoom the image to confirm the position to be measured in detail.

Use of the blood vessel visualizing light source 3 and the blood vessel detecting device 4 allows vividly displaying a blood vessel on the monitor 10 even when the blood vessel is a capillary difficult to view by naked eyes, so that the user can measure without considering the size of a blood vessel and the distance of the blood vessel from skin surface. If the portion to be measured can be viewed by naked eyes, the blood vessel visualizing light source 3 and the blood vessel detecting device 4 may not be used.

The user can confirm the position to be measured by viewing the blood vessel image displayed on the monitor 10, and then cause the ends of the optical fibers 7 to touch the position. Thus, the touched position is irradiated with excitation light from the excitation light source 8. At that time, by measuring fluorescence while causing the monitor to display the image captured by the blood vessel detecting device 4, the user can comprehend the position to be measured in real time. Examples of a light source usable as the excitation light source 8 include light bulbs such as halogen and xenon light sources, LED, and LD. The optical fibers 7 are used to conduct excitation light to the portion to be analyzed with as small loss as possible. A converging lens (lens mechanism 13 in FIG. 8) may be used instead of the optical fibers 7 in order to converge and radiate light from the excitation light source.

The blood vessel position to be measured is irradiated with light from the optical fibers 7 to excite fluorescence, which is conducted to the detector 9 via the optical fiber positioned concentrically with the optical fibers 7 used in the irradiation. Examples of the device for detecting fluorescence include semiconductor detectors such as a CCD array and a CMOS imaging sensor, a photomultiplier tube (PMT), and a channeltron detector. In consideration of portability, the semiconductor detector is advantageous.

Figure 4:
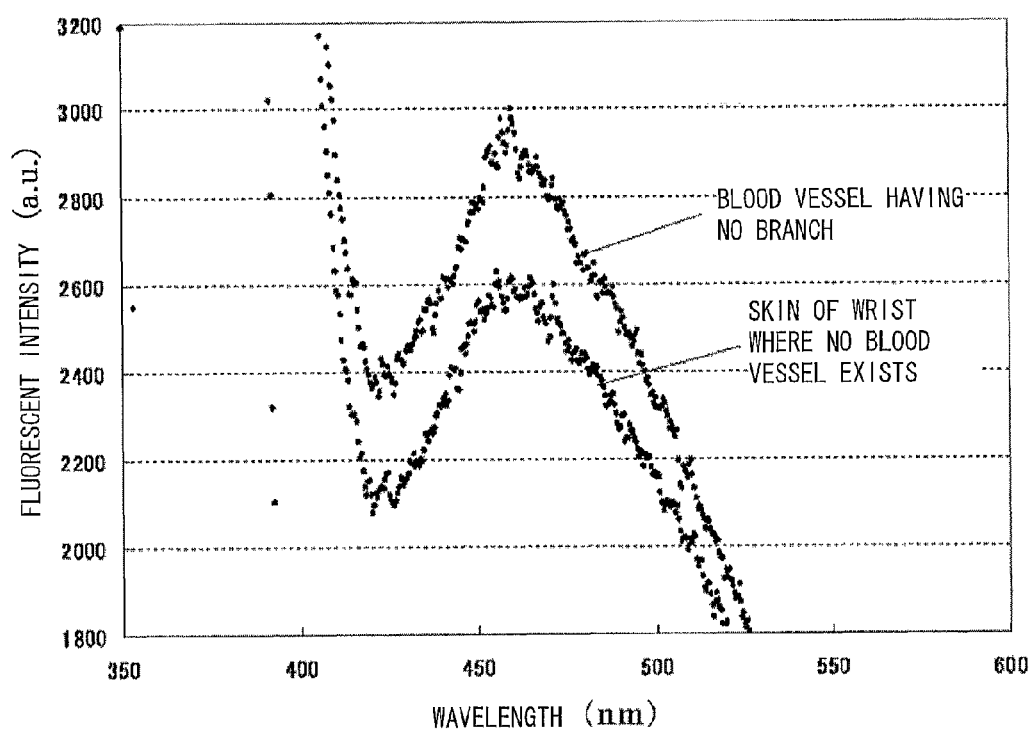
FIG. 4 is a graph showing a result of analysis by the device for monitoring blood vessel conditions in accordance with the embodiment.

The result of the detector 9's reception of the fluorescence excited from the blood vessel is displayed by the monitor 10 as fluorescent spectrum shown in FIG. 4 for example. Alternatively, fluorescent intensity at a predetermined wavelength may be displayed as a numeral by the monitor 10. The control device 5 is preferably, for example, a personal computer capable of adjusting luminance of the excitation light source 8, controlling radiation/non-radiation, displaying and analyzing the obtained fluorescent spectrum, and storing the obtained data.

In actual use, the position of a blood vessel is visualized through the above procedures, and then the position is irradiated with light for exciting AGEs, so that the health condition of the tissue of an individual, the health condition of the blood vessel in particular, can be determined based on the obtained fluorescent intensity. In order to irradiate the position with excitation light for AGEs based on the blood vessel image, it is desirable that the device of the present invention includes a mechanism for radiating excitation light precisely by using a mechanical positioning mechanism (manipulator) 11 capable of moving the optical fiber 7 in x-, y-, and z-directions.

Figure 8:
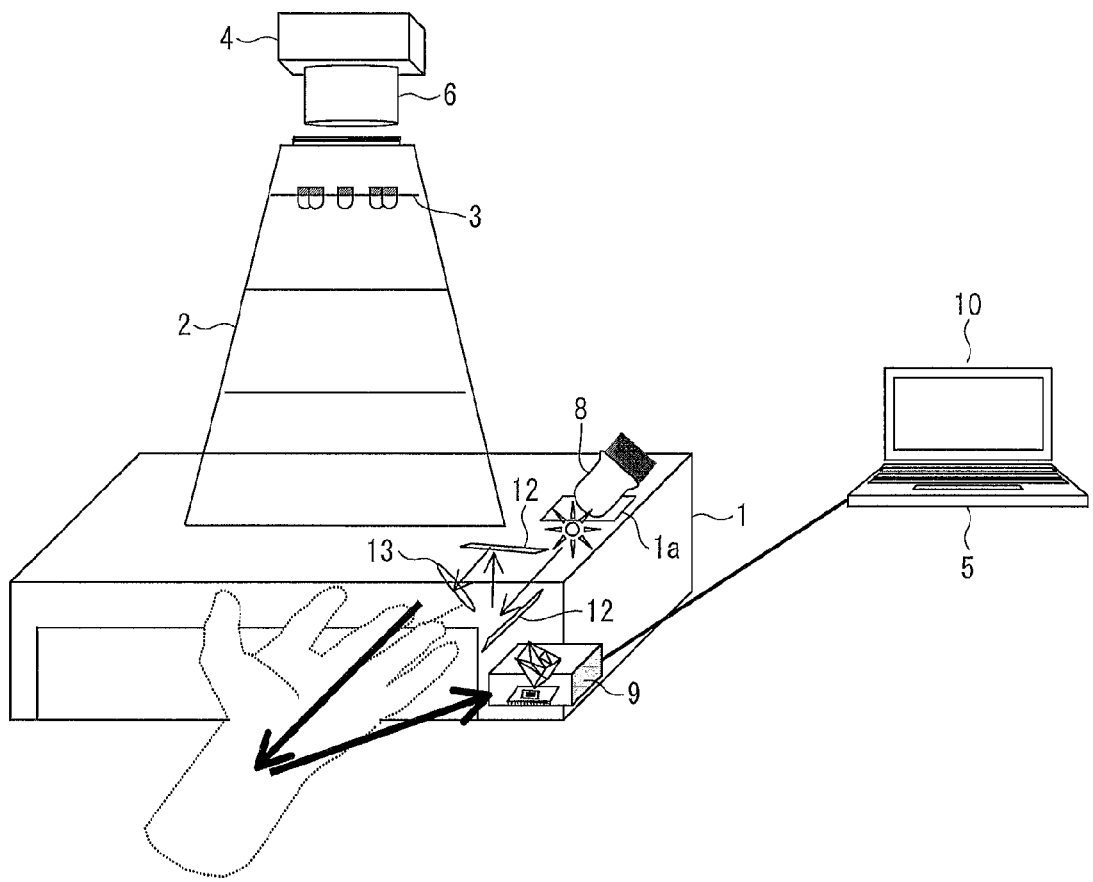
FIG. 8 is a view schematically showing another example of a device for monitoring blood vessel conditions in accordance with the embodiment.

Alternatively, as shown in FIG. 8, a converging lens (lens mechanism 13) may be provided inside the light-shielding case 1 and the control device 5 may have a mechanism for controlling the focusing position of the converging lens. Furthermore, there may be provided inside the light-shielding case 1 a mirror mechanism 12 for conducting light radiated from the excitation light source 8 via a light conducting hole 1a and radiating the light. The control device 5 may have a mechanism for controlling the position, angle etc. of the mirror mechanism 12. Furthermore, the detector 9 may include a spectrograph, thereby splitting light to detect fluorescent intensity at a specific wavelength. Available wavelength of the spectrograph is not particularly limited. Since it is evident that fluorescence has a wavelength with lower energy than that of excitation light, the spectrograph should be capable of splitting light with a wavelength of 320 to 900 nm.

With reference to measurement examples, the following explains the present invention in more details.

Measurement Example 1

FIG. 4 shows the result of confirming the position of a blood vessel tissue and measuring AGEs at two positions, a blood vessel and skin of a wrist where no blood vessel exists, by using a device for monitoring blood vessel conditions. Herein, the blood vessel detecting device 4 is not used, and the positions of the blood vessels were confirmed by naked eyes, and the position of a blood vessel having no branch and the position of skin of a wrist where no blood vessel exists were determined. Since blood vessel having no branch is large unlike a capillary, it is easy to confirm the position of a blood vessel by naked eyes. The optical fibers 7 were caused to touch the positions thus determined, and the excitation light source 8 for AGEs radiated excitation light.

The excitation light source 8 radiated light for approximately 5 to 30 sec to excite fluorescence, which was received by the detector 9. The result is shown in FIG. 4. In FIG. 4, a horizontal axis indicates fluorescent wavelength (nm) and a longitudinal axis indicates fluorescent intensity (a.u.). The detector 9 used herein was a CCD array of 2048 pixels.

The result of detection was analyzed using the control device 5 and subjected to data processing. The result of analysis was displayed by the monitor 10 as fluorescent spectra shown in FIG. 4.

For example, comparison in fluorescent intensity at a wavelength of 460 nm between skin of a wrist where no blood vessel exists and a blood vessel having no branch shows that the former was approximately 2600 a.u. whereas the latter was approximately 3000 a.u., which indicates that fluorescent intensity is higher at the blood vessel than at the skin where no blood vessel exists. That is, when discussing whether a patient develops diabetes or not by measuring AGEs, there is a possibility that the amount of detected AGEs is so small that reliable data cannot be obtained depending on the position to be analyzed, and it is easier to detect AGEs at blood vessels than at skin, so that the measurement at blood vessels allows more precise comprehension of data transition.

Data of AGEs obtained by measuring a blood vessel as above is related to vascular endothelial function, and therefore can be used as an index for the health conditions of blood vessels. Furthermore, by storing daily data in the control device 5 etc. and monitoring the data, it is possible to improve vascular endothelial function by improving diets and improving habitual exercise for example.

Measurement Example 2

Furthermore, measurement of fluorescence from AGEs at a blood vessel was studied in detail. The following explains how the measurement was made. Fluorescent spectra from AGEs at a fingertip of a hand (fingertip), a portion of a wrist where blood vessels branch (position of a wrist where blood vessels branch), a portion of a wrist where no blood vessel exists (position of a wrist where no blood vessel is found), and a palm (position where no blood vessel is found) were measured. In the present example, in order to measure fine blood vessels, blood vessels were detected using the blood vessel visualizing light source 3 and the blood vessel detecting device 4.

Initially, under control of the control device 5, the blood vessel visualizing light source 3 radiated light to a fingertip of a hand (fingertip), the blood detecting device 4 for detecting the condition of a blood vessel of the fingertip of a hand (fingertip) to capture a blood vessel image, and the monitor 10 displayed the image. While viewing the image, a user specified the position to be irradiated with excitation light and moved the optical fibers 7 to the position. The excitation light source 8 used herein was an LED of 365 nm. An optical fiber probe having a coaxial incidence/reflection system of 1800 $\mu m \phi$ was used. The optical fibers 7 were connected with the excitation light source 8 via an SMA connector. The fiber probe was moved by a manipulator to the position to be analyzed, and excitation light from the excitation light source 8 was radiated via the optical fibers 7 to the position to be analyzed.

Fluorescence was propagated via the coaxial reflection system optical fiber to the detector 9, and fluorescent spectrum from a blood vessel of a fingertip of a hand (fingertip) was detected.

Use of the optical fibers 7 having the coaxial incidence/reflection system allows simultaneously radiating excitation light to the position to be measured and detecting fluorescence from the position while fixing the position of the optical fibers 7.

As described above, radiation of excitation light to the position to be measured may be made in such a manner that excitation light is converged by an LED with a lens or a ultraviolet converging lens and radiated while controlling the focus point.

Similarly, fluorescent spectra from AGEs at the portion of a wrist where blood vessels branch (position of a wrist where blood vessels branch), the portion of a wrist where no blood vessel exists (position of a wrist where no blood vessel is found), and the palm (position where no blood vessel is found) were measured.

Figure 5:
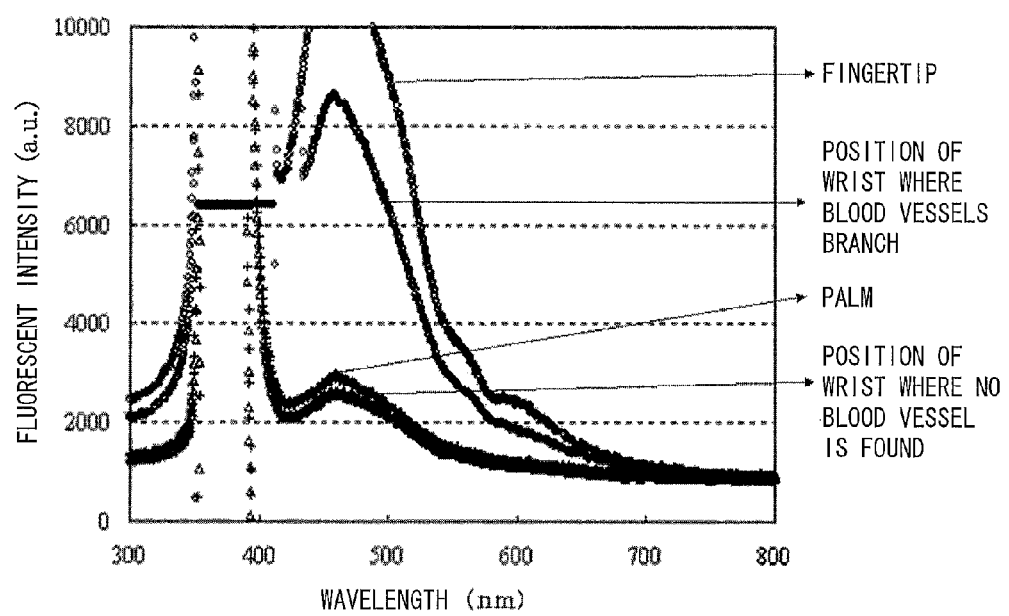
FIG. 5 is a graph showing a result of analysis by the device for monitoring blood vessel conditions in accordance with the embodiment.

FIG. 5 shows the result of measurement. In FIG. 5, a lateral axis indicates fluorescent wavelength (nm) and a longitudinal axis indicates fluorescent intensity (a.u.). For example, fluorescent intensity at the wavelength of 460 nm was 10,000 a.u. or more at the fingertip of a hand (fingertip), and approximately 9,000 a.u. at the portion of a wrist where blood vessels branch (position of a wrist where blood vessels branch), which were prominent fluorescent spectra. On the other hand, at the palm (position where no blood vessel is found) and the portion of a wrist where no blood vessel exists (position of a wrist where no blood vessel is found), fluorescent spectra were obtained, but were not large compared with the fluorescent spectra at the fingertip of a hand (fingertip) and the portion of a wrist where blood vessels branch (position of a wrist where blood vessels branch). This shows that fluorescent intensity varies greatly depending on the position to be analyzed.

When comparing fluorescent intensity between respective positions, the device may include a fluorescent material serving as a reference. An example of the fluorescent material serving as a reference is fluorescein sodium. Fluorescein sodium exhibits fluorescent wavelength of approximately 510 nm in response to the excitation light of 365 nm. Fluorescent spectrum may be standardized based on a diluted aqueous solution of approximately several % of fluorescein sodium. Alternatively, fluorescein sodium may be in the solid form instead of the diluted aqueous solution to serve as a reference material. Whether fluorescence from a portion to be measured is more intensive or less intensive than the fluorescent material serving as a reference can be an index for the measurement.

As described above, it was found that AGEs are more likely to be accumulated at the fingertip of a hand (fingertip) and a portion of a wrist where blood vessels branch (position of a wrist where blood vessels branch). That is, by measuring the position where AGEs are more likely to be accumulated, it is possible to obtain more precise and exact data.

Furthermore, in consideration of the above result, a detector which is smaller in size and lower in exactness of detection may be used. Although such a detector has sensibility lower by several times than that of the aforementioned CCD detector, limiting the purpose of measurement to confirmation of presence/absence of AGEs alone and limiting the position to be measured to a fingertip alone enable such a detector to monitor blood vessel conditions. Thus, it is possible to provide a cost-effective device for monitoring blood vessel conditions.

Measurement Example 3

AGEs may be measured while identifying the kind of a blood vessel (whether an artery or a vein) by using a difference in absorbency at a red or infrared region between oxyhemoglobin binding to oxygen (oxygenated hemoglobin) and deoxyhemoglobin not binding to oxygen (reduced hemoglobin) as means for visualizing the blood vessel.

Figure 6:
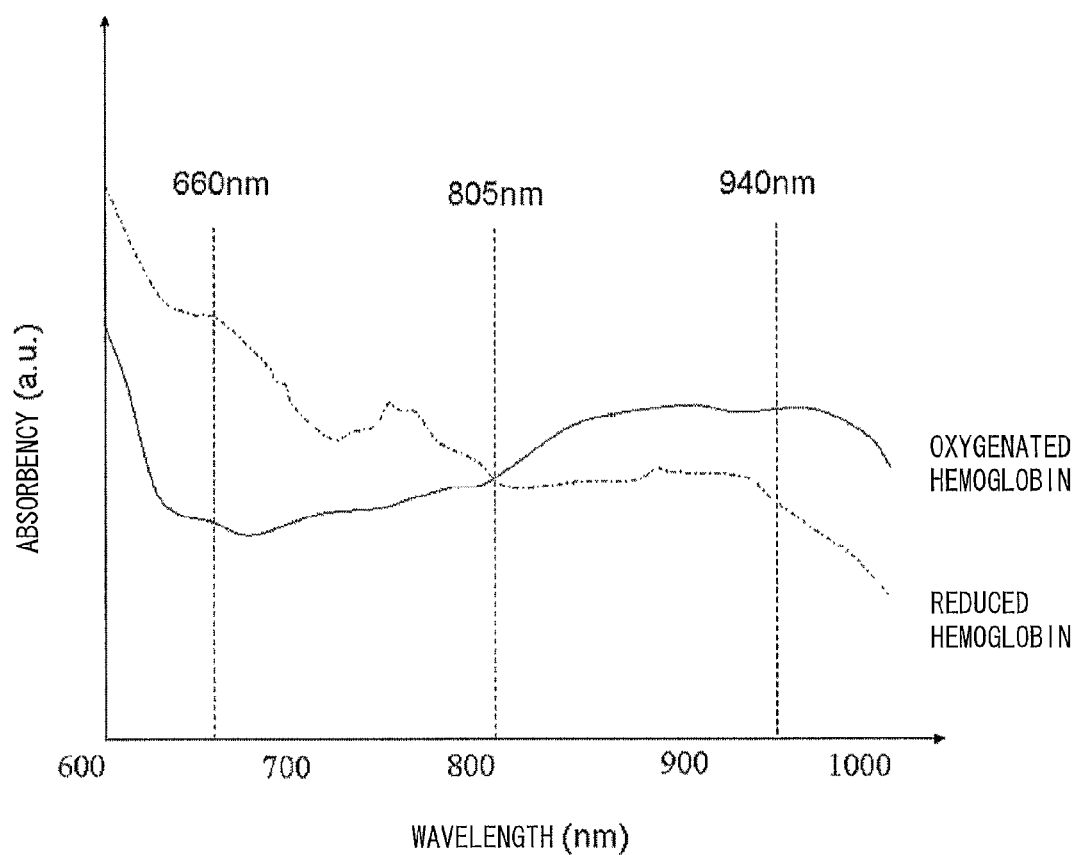
FIG. 6 is a graph showing a relation between wavelength and absorbency with respect to hemoglobin.

The following explains the embodiment. A vein contains a large amount of reduced hemoglobin, whereas an artery contains a large amount of oxygenated hemoglobin. FIG. 6 shows relations between wavelengths and absorbencies with respect to oxygenated hemoglobin and reduced hemoglobin. The horizontal axis indicates a wavelength (nm) and the longitudinal axis indicates absorbency (a.u.). The graph shows that reduced hemoglobin has high absorbency in a region with a wavelength shorter than 805 nm and oxygenated hemoglobin has high absorbency in a region with a wavelength longer than 805 nm.

That is, by radiating light with a wavelength longer than 805 nm from the blood vessel visualizing light source 3 and detecting fluorescence by the blood vessel detecting device 4, a blood vessel containing a larger amount of oxygenated hemoglobin (artery) is more clearly displayed by the monitor 10 than a blood vessel with a smaller amount of oxygenated hemoglobin (vein), so that a user can confirm the blood vessel. Subsequently, by radiating light with a wavelength shorter than 805 nm, the blood vessel containing a larger amount of oxygenated hemoglobin, which has been observed clearly, i.e. the blood vessel containing a smaller amount of reduced hemoglobin (artery), becomes unclear, whereas the blood vessel containing a larger amount of reduced hemoglobin, i.e. the blood vessel containing a smaller amount of oxygenated hemoglobin (vein) becomes clear.

As described above, radiation of light with different wavelengths changes vividness of a blood vessel image. Accordingly, by using a relative difference in absorbency between a long wavelength and a short wavelength, it is possible to visualize reduced hemoglobin and oxygenated hemoglobin, i.e. vein and artery, in such a manner that they are distinguished from each other. That is, by using a wavelength at which absorbency of oxygenated hemoglobin is higher than that of reduced hemoglobin and a wavelength at which absorbency of oxygenated hemoglobin is lower than that of reduced hemoglobin, it is possible to identify a vein and an artery. In consideration of the data of FIG. 6, use of light with a wavelength longer than 805 nm and light with a wavelength shorter than 805 nm is preferable for identifying a vein and an artery.

In view of the above, by using two or more kinds of wavelengths in a range of 600 to 1000 nm for the blood vessel visualizing light source 3, it is possible to visualize a vein and an artery in such a manner that they are distinguished from each other. It is evident from the graph of FIG. 6 that this wavelength range (600 to 1000 nm) allows distinguishing a vein and an artery from each other. FIG. 6 is a graph showing differences in absorbency between wavelengths with respect to each of oxygenated hemoglobin and reduced hemoglobin. At and around a wavelength of 660 nm, reduced hemoglobin exhibits high absorbency and reduced hemoglobin exhibits low absorbency, and the difference between the absorbencies is large. On the other hand, at and around a wavelength of 940 nm, oxygenated hemoglobin exhibits high absorbency and oxygenated hemoglobin exhibits low absorbency, and the difference between the absorbencies is large. Therefore, it is possible to detect reduced hemoglobin and oxygenated hemoglobin separately by switching the excitation light source between 660 nm and 940 nm in wavelength.

Specifically, using a near-infrared light source of a near-infrared region at and around 940 nm for detecting oxygenated hemoglobin and a light source of a red region at and around 660 nm for detecting reduced hemoglobin, light with two kinds of wavelengths is radiated to the same portion, blood vessel images capturing the portion were compared with each other to identify an artery and a vein.

Furthermore, positioning a plurality of light sources with different wavelengths and controlling a switch, the light sources can be used as light sources with different wavelengths.

An example of the blood vessel visualizing light source 3 is a Multi-Wavelength LED KED694M31D manufactured by Kyosemi Corporation. The blood vessel detecting device 4 is ⅓ CMOS (number of valid pixels 1600×1200) manufactured by SHIMADZU RIKA CORPORATION, and a 10-times magnification lens was connected in front of the CMOS.

For example, assume that absorbent spectrum is obtained from a blood vessel in response to light of a near-infrared region whose center wavelength is 940 nm, and then the blood vessel visualizing light source 3 is switched to an LED whose center wavelength is 660 nm. In a case where absorbency at 660 nm is higher and the blood vessel image is clearer, the blood vessel can be determined as a vein containing reduced hemoglobin. The method and procedure for subsequent measurements are the same as those in Measurement examples 1 and 2 above.

As described above, the present invention allows measurement by identifying the kind of a blood vessel (whether vein or artery), and allows detection of fluorescence from a material uniquely appearing or being uniquely stored in the vein or the artery. Thus, the present invention allows monitoring a specific disease derived from a material uniquely and prominently appearing or being uniquely stored in the vein or the artery.

Consequently, use of the device of the present invention for monitoring blood vessel conditions allows detecting AGEs from a blood vessel in a non-invasive manner and obtaining reliable data closely related to vascular endothelial functions, thereby allowing any user to easily and daily monitor health conditions of blood vessels. Furthermore, storing the data in a control device such as a personal computer and graphically presenting the data allow any user to easily comprehend daily health conditions. Thus, the data can be used not only for individuals' health managements but also for diagnosis at medical institutions. Accordingly, the present invention is highly expected to deal with cardiovascular function disorders such as diabetes and arteriosclerosis or motivate a user to deal with the cardiovascular function disorders.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

The present invention may be expressed as follows.

The device of the present invention is arranged such that the fluorescence from the blood vessel tissue excited by the excitation light source is fluorescence derived from an end product of the Maillard reaction (AGEs).

The device of the present invention is arranged such that the fluorescence from the blood vessel tissue excited by the excitation light source comes from a specific position of the blood vessel.

The device of the present invention is arranged so as to further include an optical fiber cable which coaxially conducts light from the excitation light source for exciting the blood vessel tissue of the living body and fluorescence from the blood vessel tissue excited by the excitation light source.

By using the optical fiber cable having a coaxial incidence/reflection system, it is possible to irradiate a position to be measured with excitation light and to detect fluorescence from the position simultaneously.

The device of the present invention is arranged so as to further include blood vessel visualizing means for specifying a position of the blood vessel tissue.

With the arrangement, even when the position to be measured includes capillaries difficult to see by naked eyes, the blood vessel visualizing means visualizes the position to be measured, so that blood vessels in the position to be measured become clear enough to be seen by naked eyes. Consequently, the user can confirm the position to be measured by seeing the position of a blood vessel, and then cause the ends of the optical fiber cable to touch the position to be measured. Thus, visualizing blood vessels allows a user to more surely cause the end of the cable to touch the position of a blood vessel to be measured. Furthermore, the user can measure more precisely at the position of the blood vessel without considering the size of the blood vessel and the distance of the blood vessel from skin surface.

The device of the present invention is arranged so as to further include mechanical positioning means (manipulator) for specifying, based on a blood vessel image visualized by the blood vessel visualizing means, a position to be analyzed, and irradiating the specified position with excitation light.

Use of the manipulator allows mechanically determining which position of the measurement target the end of the optical fiber cable is to touch (position to be measured), so that it is possible to prevent variations in the position to be measured every time the measurement is made.

The device of the present invention may be arranged so as to further include a lens or a mirror for specifying, based on a blood vessel image visualized by the blood vessel visualizing means, a position to be analyzed, and irradiating the specified position with excitation light.

With the arrangement, the control device 5 of the device for monitoring blood vessel conditions subjects the blood vessel image visualized by the blood vessel visualizing means (image captured by the blood vessel image detecting device 4 of the blood vessel tissue irradiated by the blood vessel visualizing light source 3) to image processing so as to specify the shape of the blood vessel and the position of the blood vessel.

Furthermore, the position of the end of the fiber from which the excitation light is to be emitted or a range of irradiation where the excitation light is efficiently converged and conducted is determined.

In a case where the control device 5 determines, as a result of the image processing, that the range of irradiation with the excitation light from the optical fiber is out of the specified position of the blood vessel, the control device 5 controls the position, inclination etc. of the lens mechanism for converging the excitation light and/or the mirror mechanism 12 for conducting the excitation light.

The device of the present invention is arranged such that the blood vessel visualizing means includes a near-infrared light source for detecting oxygenated hemoglobin and a red light source for detecting reduced hemoglobin.

The device of the present invention is arranged the blood vessel visualizing means is included in a light-shielding case.

With the arrangement, the light-shielding case shields ambient light other than the excitation light radiated to the position to be measured, so that it is possible to efficiently obtain fluorescence from the position to be measured.

The device of the present invention is arranged such that the fluorescence from the blood vessel tissue excited by the excitation light source serves as an index for the living body.

The device for monitoring blood vessel conditions stores in advance correlation information indicative of relations between features of fluorescence from blood vessel tissues and indices of heath conditions of living bodies in the form of a corresponding table, a function etc. The device detects the heath condition (result) of a living body in accordance with the stored correlation information and the obtained fluorescence.

For example, in a case where correlation information indicative of relation between fluorescent intensities and the amounts of accumulated AGEs or correlation information indicative of relation between the amounts of accumulated AGEs and the degree of aging of blood vessels is stored (it should be noted that the present invention is not limited to this case), the control device 5 of the device for monitoring blood vessel conditions analyzes fluorescence to detect the degree of aging of blood vessels of the living body.

Alternatively, the control device 5 may store correlation information indicating a correspondence between high fluorescent intensity and a bad health condition and a correspondence between low fluorescent intensity and a good health condition. The control device 5 periodically (e.g. once a day) measures fluorescent intensity of the same living body under the same conditions, and determines whether the health condition is getting better or worse based on a relative change in fluorescent intensity. For example, in a case where the fluorescent intensity is changed to be higher by approximately 1.5 times or more than the fluorescent intensity one week before, the control device 5 determines that the health condition is worsened, and causes the monitor 10 to display a message which urges a user to improve the health condition.

The device of the present invention is arranged such that data of the fluorescence from the blood vessel tissue excited by the excitation light source is collected in a database.

A method of the present invention for monitoring blood vessel conditions includes the steps of: exciting a blood vessel tissue of a living body; and detecting fluorescence from the excited blood vessel tissue.

INDUSTRIAL APPLICABILITY

Use of the device of the present invention for monitoring blood vessel conditions allows detecting AGEs from a blood vessel in a non-invasive manner and obtaining reliable data closely related to vascular endothelial functions, thereby allowing any user to easily and daily monitor health conditions of blood vessels. Furthermore, storing the data in a control device such as a personal computer and graphically presenting the data allow any user to easily comprehend daily health conditions. Thus, the data can be used not only for individuals' health managements but also for diagnosis at medical institutions. Accordingly, the present invention is highly expected to deal with cardiovascular function disorders such as diabetes and arteriosclerosis or motivate a user to deal with the cardiovascular function disorders. Furthermore, the device of the present invention is applicable to health devices, medical instruments, skin-diagnosis monitors, game devices etc.

REFERENCE SIGNS LIST

1. Light-shielding case
2. Light-shielding cover
3. Blood vessel visualizing light source (blood vessel visualizing unit)
4. Blood vessel detecting device (blood vessel visualizing unit)
5. Control device (detecting unit)
6. Lens
7. Optical fibers (optical fiber cable)
8. Excitation light source (excitation light source)
9. Detector (spectrograph, detecting unit)
10. Monitor
11. Mechanical positioning mechanism (manipulator, mechanical positioning unit)
12. Mirror (mirror mechanism)
13. Converging lens (lens mechanism)
31. Light source
32. Substrate
33. Washer
34. Screw

The invention claimed is:

1. A device for monitoring blood vessel conditions, comprising:
    an excitation light source configured to excite a blood vessel tissue, having an excitation wavelength set according to a kind of Advanced Glycation Endproduct (AGE) ranging from 315 to 400 nm, wherein AGE is a fluorescence derived from an end product produced via a nonenzymatic glycosylation reaction of protein (Maillard reaction); and
    a detector configured to detect fluorescent wavelengths according to the kind of AGE from the blood vessel tissue excited by the excitation light source,
    said device further comprising a blood vessel visualizing light source configured to specify a position of the blood vessel tissue, wherein the end product of the Maillard reaction has been accumulated as a result of a physiological reaction and the blood vessel visualizing light source switches between near-infrared light to detect oxygenated hemoglobin and red light to detect reduced hemoglobin.

2. The device as set forth in claim 1, further comprising a manipulator configured to radiate excitation light to a position to be analyzed which is specified by the detector,
    the detector specifying, based on a blood vessel image visualized by the blood vessel visualizing light source, either a fingertip or a point where blood vessels branch as a position to be analyzed, and
    the detector controlling the manipulator so that the specified position to be analyzed is irradiated with the excitation light.

3. The device as set forth in claim 1, further comprising a lens configured to converge light from the excitation light source and radiate the converged light to the blood vessel tissue,
    the detector including a mechanism configured to control a focus point of the lens,
    the detector specifying, based on a blood vessel image visualized by the blood vessel visualizing light source, either a fingertip or a point where blood vessels branch as a position to be analyzed, and the detector controlling the lens so that the specified position to be analyzed is irradiated with excitation light.

4. The device as set forth in claim 1, further comprising a manipulator configured to radiate excitation light to a position to be analyzed which is specified based on a blood vessel image visualized by the blood vessel visualizing light source.

5. The device as set forth in claim 1, further comprising a lens or a mirror configured to radiate excitation light to a position to be analyzed which is specified based on a blood vessel image visualized by the blood vessel visualizing light source.

6. The device as set forth in claim 1, wherein the fluorescence from the blood vessel tissue is either detected by the detector from a fingertip or from a point where blood vessels branch.

7. The device as set forth in claim 1, wherein the detector detects fluorescence from at least two positions, a position where no blood vessel is found and a position where blood vessel tissue is found, the position where no blood vessel is found is different from the position where blood vessel tissue is found and both positions are excited by the excitation light source.

8. The device as set forth in claim 1, wherein the excitation light source is an LED (Light Emitting Diode) or an LD (Laser Diode).

9. The device as set forth in claim 1, wherein the blood vessel visualizing light source is included in a light-shielding case.

10. The device as set forth in claim 1, further comprising an optical fiber cable which coaxially conducts light from the excitation light source configured to excite the blood vessel tissue and fluorescence from the blood vessel tissue excited by the excitation light source.

11. The device as set forth in claim 1, further comprising an index for health conditions of blood vessels, wherein the index is created using data obtained from the detected fluorescence from the blood vessel tissue excited by the excitation light source.

12. The device as set forth in claim 11, further comprising a database that stores data of the fluorescence from the blood vessel tissue excited by the excitation light source.

13. A method for monitoring blood vessel conditions, comprising:
    visualizing a blood vessel in order to specify a position of the blood vessel tissue using a blood vessel visualizing light source that switches between near-infrared light to detect oxygenated hemoglobin and red light to detect reduced hemoglobin;
    exciting a blood vessel tissue using an excitation wavelength set according to a kind of Advanced Gycation Endproduct (AGE) ranging from 315 to 400 nm, wherein AGE is a fluorescence derived from an end product produced via a nonenzymatic glycosylation reaction of protein (Maillard reaction); and
    detecting fluorescence wavelengths according to the kind of AGE from the excited blood vessel tissue,
    wherein detected fluorescence from the blood vessel tissue is fluorescence from either a fingertip or fluorescence from a point where blood vessels branch, wherein the end product of the Maillard reaction has been accumulated as a result of a physiological reaction.

14. The method as set forth in claim 13, wherein detecting fluorescence includes detecting both fluorescence from a position where no blood vessel is found, and detecting fluorescence from a position where blood vessel tissue is found, wherein the position where no blood vessel is found is different from the position where blood vessel tissue is found, and both the position where no blood vessel is found and the position where blood vessel tissue is found are excited by an excitation light source.

15. The method as set forth in claim 13, wherein exciting a blood vessel tissue includes using an excitation light source, that is an LED (Light Emitting Diode) or an LD (Laser Diode).

* * * * *